(12) United States Patent
Allred et al.

(10) Patent No.: US 7,247,022 B2
(45) Date of Patent: *Jul. 24, 2007

(54) DENTAL TRAY SYSTEM WITH RELEASABLE HOLD INNER AND OUTER DENTAL TRAYS

(75) Inventors: Peter M. Allred, Riverton, UT (US); Dan E. Fischer, Sandy, UT (US)

(73) Assignee: Ultradent Products, Inc., South Jordan, UT (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/047,150

(22) Filed: Jan. 31, 2005

(65) Prior Publication Data

US 2006/0172260 A1  Aug. 3, 2006

(51) Int. Cl.
*A61C 15/00* (2006.01)

(52) U.S. Cl. .................................. 433/216; 433/37

(58) Field of Classification Search ............. 433/215, 433/37, 38, 45, 47, 80, 214, 216
See application file for complete search history.

(56) References Cited

U.S. PATENT DOCUMENTS

| | | | | |
|---|---|---|---|---|
| 2,092,097 | A | * | 9/1937 | Town .......................... 433/184 |
| 2,835,628 | A | | 5/1958 | Saffir |
| 3,527,219 | A | * | 9/1970 | Greenberg .................... 433/25 |
| 3,688,406 | A | * | 9/1972 | Porter et al. ............. 433/217.1 |
| RE33,093 | E | | 10/1989 | Schiraldi et al. |
| 5,059,120 | A | | 10/1991 | Lee |
| 5,076,791 | A | | 12/1991 | Madray, Jr. |
| 5,165,424 | A | | 11/1992 | Silverman |
| 5,326,685 | A | | 7/1994 | Gaglio et al. |
| 5,460,527 | A | * | 10/1995 | Kittelsen .................... 433/215 |
| 5,562,449 | A | | 10/1996 | Jacobs et al. |
| 5,573,399 | A | | 11/1996 | McClintock, II |
| 5,616,027 | A | * | 4/1997 | Jacobs et al. ................. 433/37 |
| 5,707,235 | A | | 1/1998 | Knutson |
| 5,769,633 | A | | 6/1998 | Jacobs et al. |
| 5,816,802 | A | | 10/1998 | Montgomery |
| 5,879,691 | A | | 3/1999 | Sagel et al. |
| 5,891,453 | A | | 4/1999 | Sagel et al. |
| 5,894,017 | A | | 4/1999 | Sagel et al. |
| 5,924,863 | A | | 7/1999 | Jacobs et al. |
| 5,989,569 | A | | 11/1999 | Dirksing et al. |
| 6,045,811 | A | | 4/2000 | Dirksing et al. |
| 6,089,869 | A | | 7/2000 | Schwartz |

(Continued)

*Primary Examiner*—Ralph A. Lewis
(74) *Attorney, Agent, or Firm*—Workman Nydegger

(57) ABSTRACT

A dental treatment system used to treat (e.g., bleach) a person's teeth. The inventive system includes an inner dental treatment tray having a tray configuration so as to fit over at least a portion of a person's upper or lower dental arch. The inner dental treatment tray is sufficiently thin and flexible so as to at least partially conform to a person's teeth without heating when used in combination with a dental treatment and/or adhesive composition. The dental treatment system includes an outer support tray positioned adjacent to the inner dental treatment tray so as to maintain the inner dental treatment tray in the tray configuration prior to placement of the inner dental treatment tray over the person's teeth. The dental treatment system also includes temporary adhesion means (e.g., a weak adhesive) for maintaining the outer support tray adjacent to the inner dental treatment tray prior to and during placement of the inner dental treatment tray over the person's teeth.

22 Claims, 7 Drawing Sheets

U.S. PATENT DOCUMENTS

| | | | |
|---|---|---|---|
| 6,096,328 A | 8/2000 | Sagel et al. |
| 6,106,293 A | 8/2000 | Wiesel |
| 6,136,297 A | 10/2000 | Sagel et al. |
| 6,155,832 A | 12/2000 | Wiesel |
| 6,183,251 B1 | 2/2001 | Fischer |
| 6,197,331 B1 | 3/2001 | Lerner et al. |
| 6,274,122 B1 | 8/2001 | McLaughlin |
| 6,277,458 B1 | 8/2001 | Dirksing et al. |
| 6,280,196 B1 | 8/2001 | Berghash |
| 6,287,120 B1 | 9/2001 | Wiesel |
| 6,309,625 B1 | 10/2001 | Jensen et al. |
| 6,322,360 B1 | 11/2001 | Burgio |
| 6,343,932 B1 | 2/2002 | Wiesel |
| 6,364,665 B1 | 4/2002 | Trettenero |
| 6,382,979 B2 | 5/2002 | Lindquist |
| 6,419,903 B1 | 7/2002 | Xu et al. |
| 6,419,906 B1 | 7/2002 | Xu et al. |
| 6,435,873 B1 | 8/2002 | Burgio |
| 6,440,396 B1 | 8/2002 | McLaughlin |
| 6,461,158 B1 | 10/2002 | Sagel et al. |
| 6,500,408 B2 | 12/2002 | Chen |
| 6,503,486 B2 | 1/2003 | Xu et al. |
| 6,514,483 B2 | 2/2003 | Xu et al. |
| 6,514,484 B2 | 2/2003 | Rajaiah et al. |
| 6,551,579 B2 | 4/2003 | Sagel et al. |
| 6,607,382 B1 | 8/2003 | Kuo et al. |
| 6,638,496 B2 | 10/2003 | McLaughlin |
| 6,649,147 B1 | 11/2003 | Ye et al. |
| 6,682,721 B2 | 1/2004 | Kim et al. |
| 6,689,344 B2 | 2/2004 | Chang et al. |
| 6,730,316 B2 | 5/2004 | Chen |
| 2002/0006387 A1 | 1/2002 | Sagel et al. |
| 2002/0006388 A1 | 1/2002 | Sagel et al. |
| 2002/0012685 A1 | 1/2002 | Sagel et al. |
| 2002/0018754 A1 | 2/2002 | Sagel et al. |
| 2002/0081555 A1 | 6/2002 | Wiesel |
| 2002/0164292 A1 | 11/2002 | Peterson et al. |
| 2002/0182154 A1 | 12/2002 | McLaughlin |
| 2002/0187111 A1 | 12/2002 | Xu et al. |
| 2002/0187112 A1 | 12/2002 | Xu et al. |
| 2003/0003421 A1 | 1/2003 | Besenheider et al. |
| 2003/0012747 A1 | 1/2003 | Peterson |
| 2003/0044631 A1 | 3/2003 | Sagal et al. |
| 2003/0068284 A1 | 4/2003 | Sagel et al. |
| 2003/0082114 A1 | 5/2003 | Kim et al. |
| 2003/0133884 A1 | 7/2003 | Chang et al. |
| 2003/0152884 A1* | 8/2003 | Wiechmann et al. .......... 433/9 |
| 2003/0194382 A1 | 10/2003 | Chang et al. |
| 2003/0198606 A1 | 10/2003 | Kim et al. |
| 2004/0002034 A1 | 1/2004 | Jacobs et al. |
| 2004/0002035 A1 | 1/2004 | Jacobs et al. |
| 2004/0038183 A1 | 2/2004 | Jacobs et al. |
| 2004/0146836 A1* | 7/2004 | Andersen .................... 433/215 |
| 2004/0146837 A1 | 7/2004 | Andersen |
| 2004/0214140 A1 | 10/2004 | Fischer et al. |
| 2004/0234929 A1* | 11/2004 | Fischer et al. ............. 433/215 |
| 2004/0241618 A1 | 12/2004 | Allred et al. |
| 2004/0242620 A1 | 12/2004 | Allred et al. |
| 2005/0186150 A1* | 8/2005 | Allred et al. ................. 424/53 |
| 2005/0186539 A1* | 8/2005 | McLean et al. ............. 433/215 |
| 2005/0249667 A1* | 11/2005 | Tuszynski et al. ........... 424/9.3 |

* cited by examiner

DENTAL TRAY SYSTEM WITH RELEASABLE HOLD INNER AND OUTER DENTAL TRAYS

BACKGROUND OF THE INVENTION

1. The Field of the Invention

The present invention is in the field of dental tray shaped devices used to provide a desired dental treatment to a person's teeth. The device can be used for dental treatments such as bleaching, administration of fluoride, or application of other medicines.

2. The Relevant Technology

Virtually all people desire white or whiter teeth. To achieve this goal, people have veneers placed over their teeth or have their teeth chemically bleached. A common bleaching method involves the use of a dental tray that is custom-fitted to a person's teeth and that is therefore comfortable to wear. One type of customized tray is made from a stone cast of a person's teeth. Another is customized directly using a person's teeth as a template (e.g., "boil-and-bite" trays). Non-customized trays that approximate the shapes and sizes of a variety of users' dental arches have also been used. A dental bleaching composition is placed into the tray and the tray placed over the person's teeth for a desired period of time.

Ultimately, the main impediment to successful bleaching is the failure of users to complete the prescribed bleaching regimen. If the bleaching apparatus is difficult to install over a person's teeth, or is uncomfortable to wear, the user may simply give up and prematurely abort the prescribed bleaching regimen.

In view of the foregoing, there is an ongoing need for improved bleaching apparatus and methods that are comfortable and easy to use and that reliably remain in position over the user's teeth so as to reduce diffusion of bleaching composition into a user's oral cavity. Such improvements would be expected to improve or encourage compliance by the user.

BRIEF SUMMARY OF THE PREFFERED EMBODIMENTS

The present invention generally relates to a dental treatment system used to treat (e.g., bleach) a person's teeth. The inventive system includes an inner dental treatment tray having a tray configuration so as to fit over at least a portion of a person's upper or lower dental arch and that is initially nested within an outer support tray. The inner dental treatment tray is sufficiently thin and flexible so as to at least partially conform to a person's teeth without heating when used in combination with a dental treatment and/or adhesive composition. The treatment tray defines an interior trough having an exterior opening through which a treatment composition and the person's teeth can be inserted.

The dental treatment system also includes an outer support tray positioned adjacent to the inner dental treatment tray so as to maintain the inner dental treatment tray in the tray configuration prior to and that assists the user in placing the inner dental treatment tray over the person's teeth. Also included is temporary adhesion means for maintaining the outer support tray adjacent to the inner dental treatment tray prior to and during placement of the inner dental treatment tray over the person's teeth.

According to one embodiment, the temporary adhesion means comprises a weak adhesive between the inner dental treatment tray and the outer support tray. The weak adhesive may be hydrophobic or water soluble, as desired. A hydrophobic weak adhesive may more easily spread over the materials of the outer support tray and the inner dental treatment tray. A water soluble weak adhesive may be more easily removed, e.g., by rinsing, after placement. Examples of suitable weak adhesives include glycerin, polyethylene glycol, adhesive silicons, petrolatum, oils (e.g., mineral oil), sticky polymers in water or another solvent (e.g., glycerin or a glycol), or sticky resins.

The inner dental treatment tray is formed from a moisture-resistant polymer material, examples of which include polyolefins, polyesters, ethylene-vinyl acetate copolymer (EVA), polyurethane, other polymers, and blends thereof (e.g., polyethylene and polypropylene). The inner dental treatment tray is sufficiently thin and flexible so that it will at least partially conform to the person's dental arch without any heating of the tray. According to one embodiment, the inner dental treatment tray preferably has a thickness ranging from about 0.01 mm to about 1.5 mm, more preferably ranging from about 0.015 mm to about 0.5 mm, and most preferably from about 0.025 mm to about 0.2 mm.

The dental treatment system includes an outer support tray positioned adjacent to the inner dental treatment tray so as to maintain the inner dental treatment tray in the tray configuration prior to and during placement of the inner dental treatment tray over the person's teeth. The outer support tray is more rigid and generally thicker than the inner dental treatment tray. The outer support tray allows the inner dental treatment tray to be very thin and flexible, which provides an advantage in its comfort and ability to conform to the person's teeth. The outer support tray may have the same tray configuration as the inner dental treatment tray so as to receive and support the inner dental treatment tray. The outer support tray provides support and ease of placement to the dental treatment system while positioning the system over a person's teeth. In one embodiment, the outer support tray includes a handle to facilitate gripping and maneuverability of the support tray while placing the inner dental treatment tray of the system over the teeth. Once positioned, the inner dental treatment tray is removed so as to leave the inner dental treatment tray in place over the teeth.

According to one embodiment, the dental treatment system may include a treatment composition. The treatment composition may comprise a sticky viscous gel, a less viscous gel, a highly viscous putty, or a substantially solid composition that is less adhesive prior to being moistened with saliva or water but that becomes more sticky and adhesive when moistened. The treatment and/or adhesive compositions may include any desired active agent, including, but not limited to, dental bleaching agents, desensitizing agents, remineralizing agents, antimicrobial agents, anti-plaque agents, anti-tartar agents, or other medicaments.

For convenience of use, multiple dental treatment systems may be packaged together and sold as a kit. In one embodiment, the number of treatment systems provided with each kit can equal the number of sessions that represent a prescribed treatment regimen. The treatment systems can be sealed collectively or individually as desired.

These and other advantages and features of the present invention will become more fully apparent from the following description and appended claims, or may be learned by the practice of the invention as set forth hereinafter.

BRIEF DESCRIPTION OF THE DRAWINGS

To further clarify the above and other advantages and features of the present invention, a more particular description of the invention will be rendered by references to specific embodiments thereof, which are illustrated in the appended drawings. It is appreciated that these drawings depict only typical embodiments of the invention and are therefore not to be considered limiting of its scope. The invention will be described and explained with additional specificity and detail through the use of the accompanying drawings in which.

DETAILED DESCRIPTION OF THE PREFERRED EMBODIMENTS

I. Introduction and Definitions

Figure 1A:
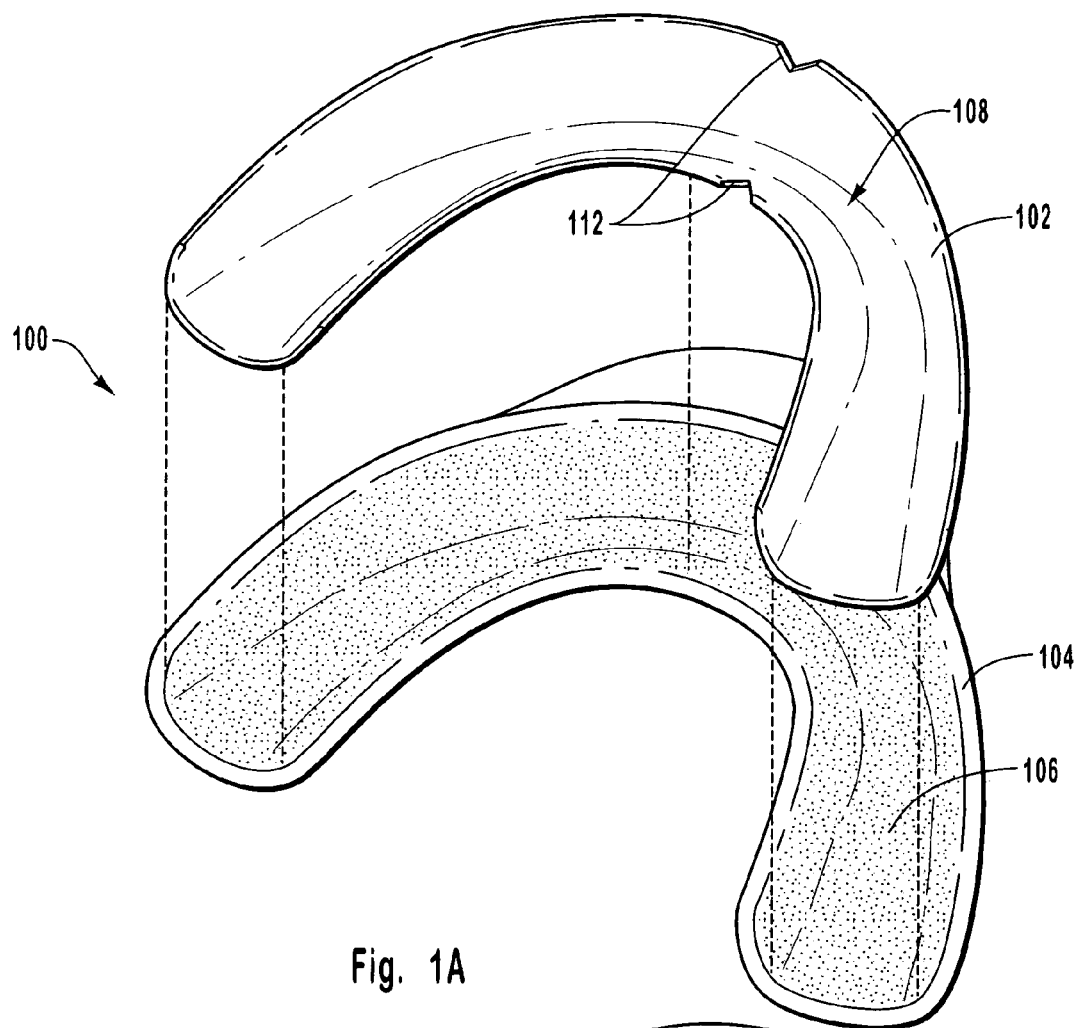
FIG. 1A is an exploded view of an exemplary dental treatment system including an inner dental treatment tray, an outer support tray, and temporary adhesion means.

The inventive dental treatment system includes an inner dental treatment tray, an outer support tray, and temporary adhesion means for maintaining the outer support tray adjacent to the inner dental treatment tray prior to and during placement of the inner dental treatment tray over a person's teeth. The inner dental treatment tray has a tray configuration so as to fit over at least a portion of a person's upper or lower dental arch. The inner dental treatment tray has a thickness and flexibility that allows it to at least partially conform to the person's teeth without heating when used in combination with a dental treatment and/or adhesive composition.

The term "molecular weight", as used herein, refers to number average molecular weight expressed in Daltons unless otherwise specified.

II. Exemplary Dental Treatment Systems

A. Inner Dental Treatment Tray

The dental treatment system includes an inner dental treatment tray having a tray configuration. The inner dental treatment tray has a tray configuration defining an interior trough with an exterior opening through which a treatment composition and the person's teeth can be inserted. The dental treatment tray is sufficiently thin and flexible so that it at least partially conforms to the person's teeth without heating when used in combination with a dental treatment and/or adhesive composition.

The inner dental treatment tray may be formed of any suitable material. Examples of materials that can be used to form the inner dental treatment tray include, but are not limited to, polyolefins, ethylene-vinyl acetate copolymer (EVA), ethylene-vinyl alcohol copolymer (EVAL), polycaprolactone (PCL), polyvinyl chloride (PVC), polyesters, polycarbonates, polyamides, polyurethanes, or polyesteramides. Examples of suitable polyolefins that can be used to make the inner dental treatment tray include, but are not limited to, polyethylene (PE), high density polyethylene (HDPE), low density polyethylene (LDPE), ultra low density polyethylene (ULDPE), polypropylene (PP), and polytetrafluoroethylene (PTFE) (e.g., TEFLON). An example of a suitable polyester for use in making the inner dental treatment tray includes, but is not limited to, polyethylene terephthalate (PET), an example of which is MYLAR, sold by DuPont. An example of a suitable polyurethane barrier material is a polyurethane film manufactured by ArgoTech, which is located in Greenfield, Mass. The inner dental treatment tray may comprise a polymeric blend comprising two or more of the foregoing materials. Plasticizers, flow additives, and fillers known in the art can be used as desired to modify the properties of any of the foregoing polymers used to form the inner dental treatment tray.

Other materials that can act as an inner dental treatment tray include cellulose esters (e.g., cellulose acetate), polyvinyl acetate, polyvinyl alcohol, shellac, water-resistant cellulosic ethers, and chemical or light-cure materials (e.g., methacrylate or acrylate resins).

The inner dental treatment tray is sufficiently thin and flexible so that it will at least partially conform to the person's teeth without any heating of the tray. According to one embodiment, the inner dental treatment tray preferably has a thickness ranging from about 0.01 mm to about 1.5 mm, more preferably ranging from about 0.015 mm to about 0.5 mm, and most preferably from about 0.025 mm to about 0.2 mm.

B. Outer Support Tray

The dental treatment system includes an outer support tray. The outer support tray is positioned adjacent to the inner dental treatment tray so as to maintain the inner dental treatment tray in the tray configuration prior to placement of the inner dental treatment tray over a person's teeth.

The outer support tray is more rigid, and generally thicker than the inner dental treatment tray, so as to allow the inner dental treatment tray to be very thin and flexible, which provides an advantage in its comfort and ability to conform to the person's teeth. The outer support tray may have the same configuration as the inner dental treatment tray so as to receive and support the inner dental treatment tray. The outer support tray provides support and ease of placement to the dental treatment system while positioning the system over a person's teeth. In one embodiment, the outer support tray includes a handle to facilitate gripping and maneuverability of the support tray while placing the inner dental treatment tray of the system over the teeth.

The outer support tray may be formed of any suitable material. Examples of suitable materials include those discussed above with respect to the inner dental treatment tray. The outer support tray is formed so as to have sufficient rigidity so as to support the inner dental treatment tray.

C. Temporary Adhesion Means

The dental treatment system includes temporary adhesion means for maintaining the outer support tray adjacent to the inner dental treatment tray prior to and during placement of the inner dental treatment tray over the person's teeth. According to one embodiment, the temporary adhesion means may comprise a weak adhesive between the inner dental treatment tray and the outer support tray. The weak adhesive may be hydrophobic or water soluble, as desired. A hydrophobic weak adhesive may more easily spread over the materials of the outer support tray and the inner dental treatment tray. A water soluble weak adhesive may be more easily removed, e.g., by rinsing, after placement. Examples of suitable weak adhesives include glycerin, polyethylene glycol, adhesive silicons, petrolatum, oils (e.g., mineral oil), sticky polymers in water or another solvent (e.g., glycerin or a glycol), or sticky resins.

D. Dental Treatment Compositions

According to one embodiment, the dental treatment system may include a treatment composition. The treatment composition may comprise a sticky viscous gel, a less viscous gel, a highly viscous putty, or a substantially solid composition that is less adhesive prior to being moistened with saliva or water but that becomes more sticky and adhesive when moistened. The treatment and/or adhesive compositions may include any desired active agent, including, but not limited to, dental bleaching agents, desensitizing agents, remineralizing agents, antimicrobial agents, antiplaque agents, anti-tartar agents, or other medicaments.

Specific dental treatment compositions and their components are disclosed in U.S. patent application Ser. No. 10/790,446, filed Feb. 19, 2004, and entitled ORAL TREATMENT DEVICES THAT INCLUDE A THIN, FLEXIBLE BARRIER LAYER AND AN ENDOSKELETON TREATMENT OR ADHESIVE COMPOSITION, which is hereby incorporated by reference with respect to its disclosure of treatment and adhesive compositions.

E. Characteristics of Dental Treatment Systems

FIG. 1A illustrates an exploded view of an exemplary dental treatment system 100. Dental treatment system 100 includes an inner dental treatment tray 102, an outer support tray 104, and a weak adhesive 106 between the inner dental treatment tray 102 and the outer support tray 104. Inner dental treatment tray 102 has a tray configuration defining an interior trough 108. The outer support tray 104 includes a handle 110. In the illustrated embodiment, weak adhesive 106 covers the interior surface of outer support tray 104. In alternative embodiments, the weak adhesive may cover all or a portion of the interior surface of the outer support tray, the exterior surface of the inner dental treatment tray, or any desired coverage combination.

The inner dental tray may include one or more notches 112. Notches 112 allow the dental treatment tray 102 to more easily spread open or compress in the area of the incisors. This may be helpful in allowing the tray 102 to more easily conform to differently-sized dental arches.

Figure 1B:
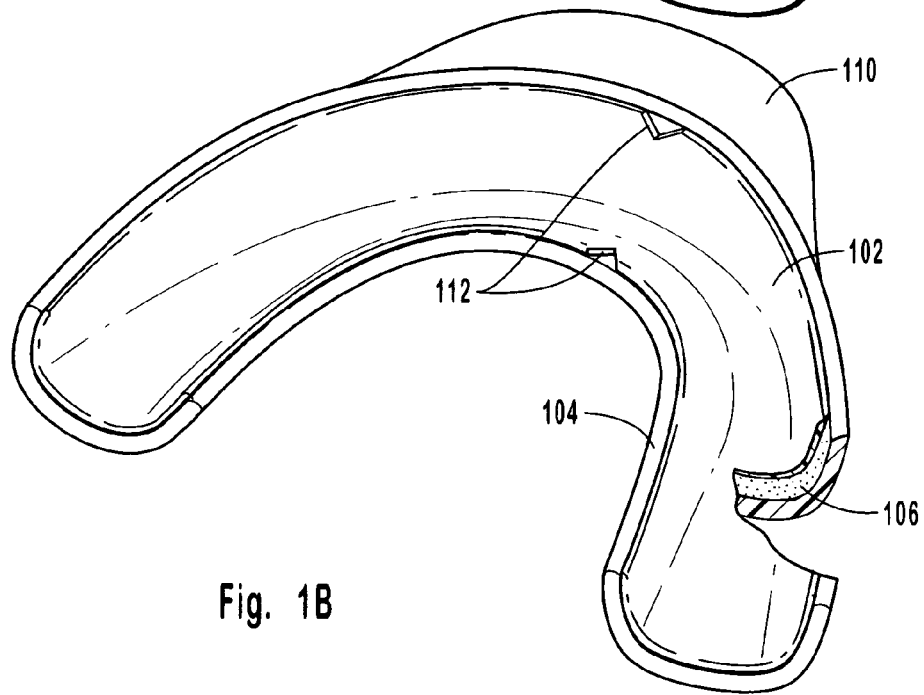
FIG. 1B is a perspective view of the dental treatment system of FIG. 1A.

FIG. 1B illustrates the assembled dental treatment system 100. A small portion of the image is cut-away so as to better illustrate weak adhesive 106 between inner dental tray 102 and outer support tray 104. The weak adhesive 106 holds the inner dental treatment tray 102 and outer support tray 104 together prior to and during placement of the inner dental tray 102 over the person's teeth.

Figure 2:
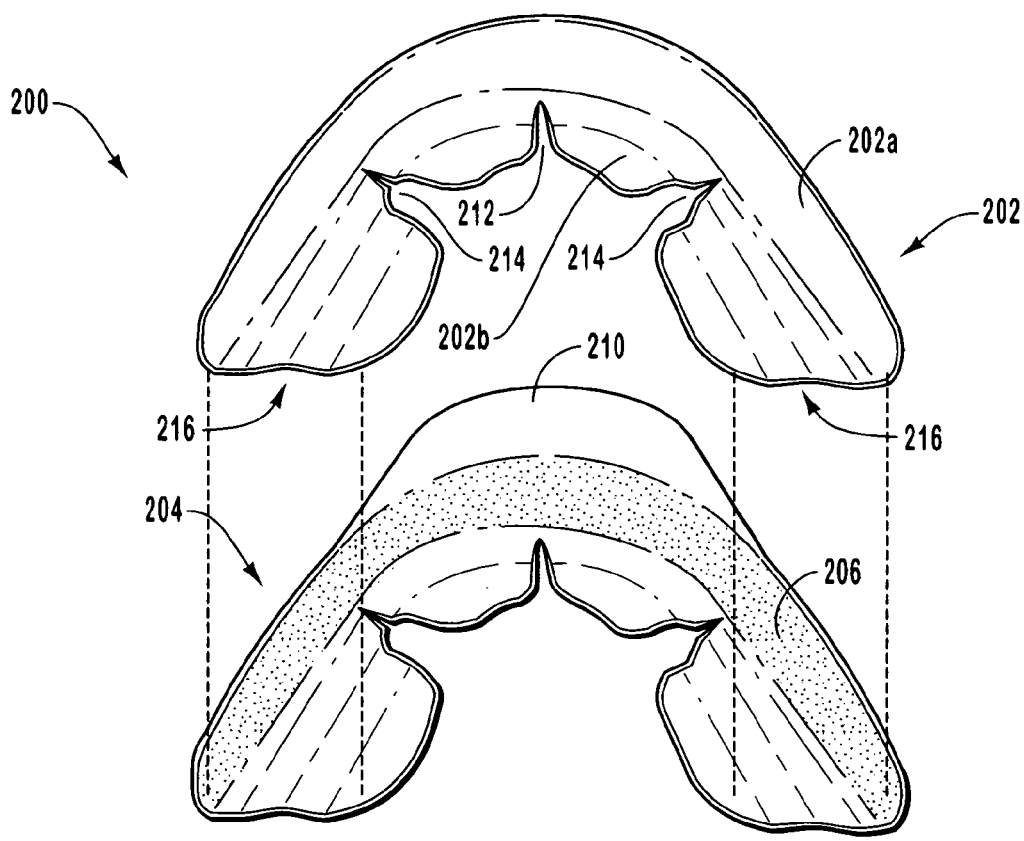
FIG. 2 is an exploded view of an alternative dental treatment system.

FIG. 2 illustrates an exploded view of an alternative embodiment of a dental treatment system 200. Dental treatment system 200 includes an inner dental treatment tray 202, an outer support tray 204, and a weak adhesive 206 between the treatment tray 202 and the support tray 204. In the illustrated embodiment, weak adhesive 206 covers a portion of the interior surface of outer support tray 204.

The inner dental treatment tray 202 has a tray configuration including a front side wall 202a and a bottom wall 202b. Bottom wall 202b includes a plurality of cuts positioned to help the bottom wall 202b better conform to abrupt changes in the diameters of a person's teeth, particularly where the bicuspids and canines meet. The cuts help to compensate for the fact that bicuspids are significantly thicker than canines by allowing for an abrupt discontinuity in the bottom wall 202b of the dental treatment system 200. In the illustrated embodiment, the cuts comprise notches 214.

The illustrated embodiment includes additional features to enhance fit. Notch 212 allows the dental treatment system 200 to more easily spread open or compress in the area of the incisors so as to more easily conform to differently-sized dental arches. Two V-shaped indentations 216 configured to be inserted into the depression typically found along the top surfaces of a person's left and right molars provide a better conformation to the teeth, resulting in a more comfortable fit. These and additional anatomical features that may be included are described in U.S. patent application Ser. No. 10/783,597, filed Feb. 19, 2004, and entitled UNIVERSAL TRAY DESIGN HAVING ANATOMICAL FEATURES TO ENHANCE FIT, which is hereby incorporated by reference with respect to its disclosure of anatomical design features.

Figure 3:
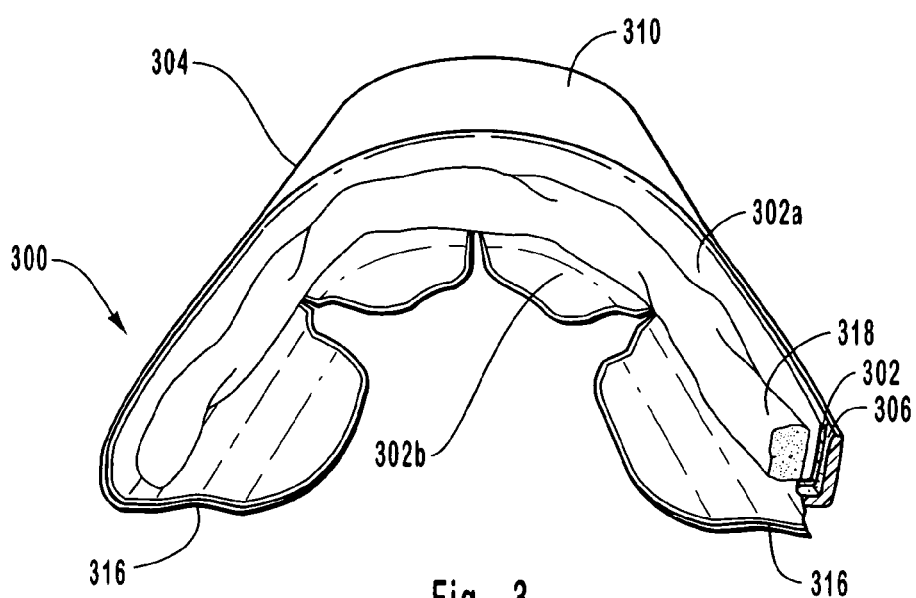
FIG. 3 is a perspective view of the dental treatment system of FIG. 2 with a dental treatment composition placed within the trough of the inner dental treatment tray.

FIG. 3 illustrates a dental treatment system 300 having an inner dental treatment tray 302 having a front side wall 302a and a bottom wall 302b. The system 300 is held within outer support tray 304 by temporary adhesion means 306. Dental treatment system 300 also includes a dental treatment composition 318 within the interior trough of inner dental treatment tray 302. Dental treatment system 300 may be pre-loaded with a dental treatment composition, or the composition may be applied later by the person.

Figure 4:
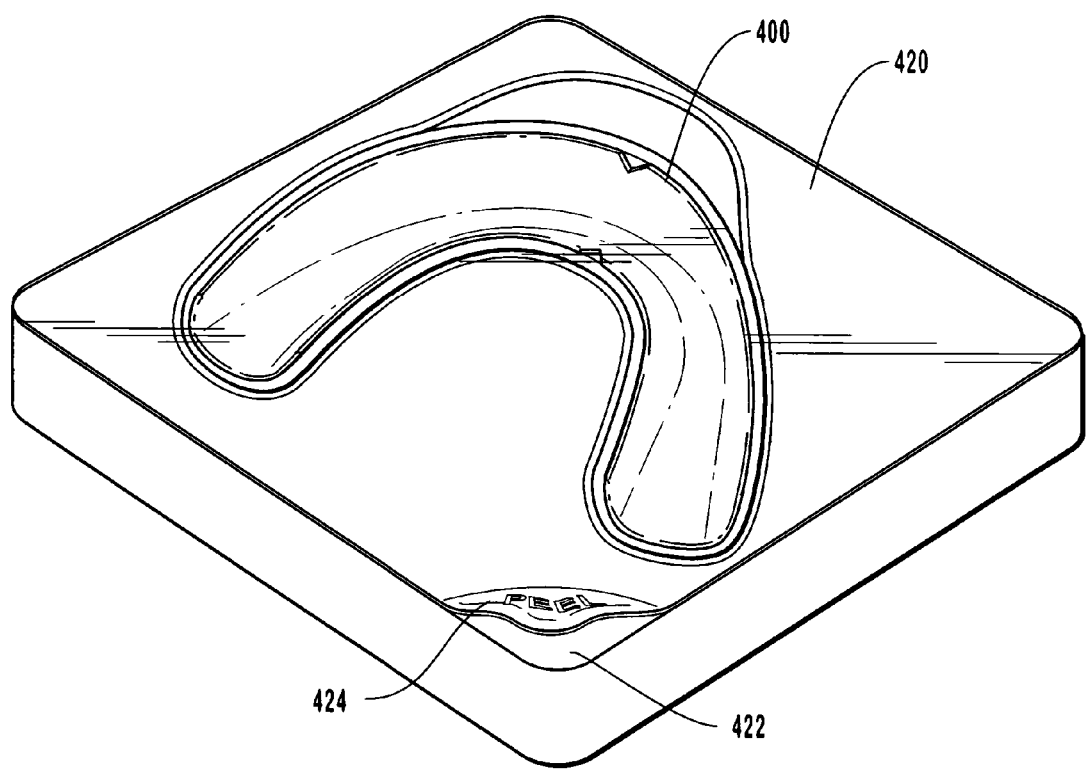
FIG. 4 illustrates an exemplary dental treatment system contained within a sealed protective package having a peelable cover.

The dental treatment system can be packaged within a sealed container or package. As illustrated in FIG. 4, the dental treatment system 400 can be sealed within a protective package 420 that includes a rigid support layer 422 and a peelable cover 424. Any embodiment of the dental treatment system can be sealed within a protective package. When it is desired to use the dental treatment system 400, the peelable cover 424 is removed and the dental treatment system 400 is removed or separated from the support layer 422.

III. Exemplary Methods of Using Dental Treatment Systems

Figure 5A:
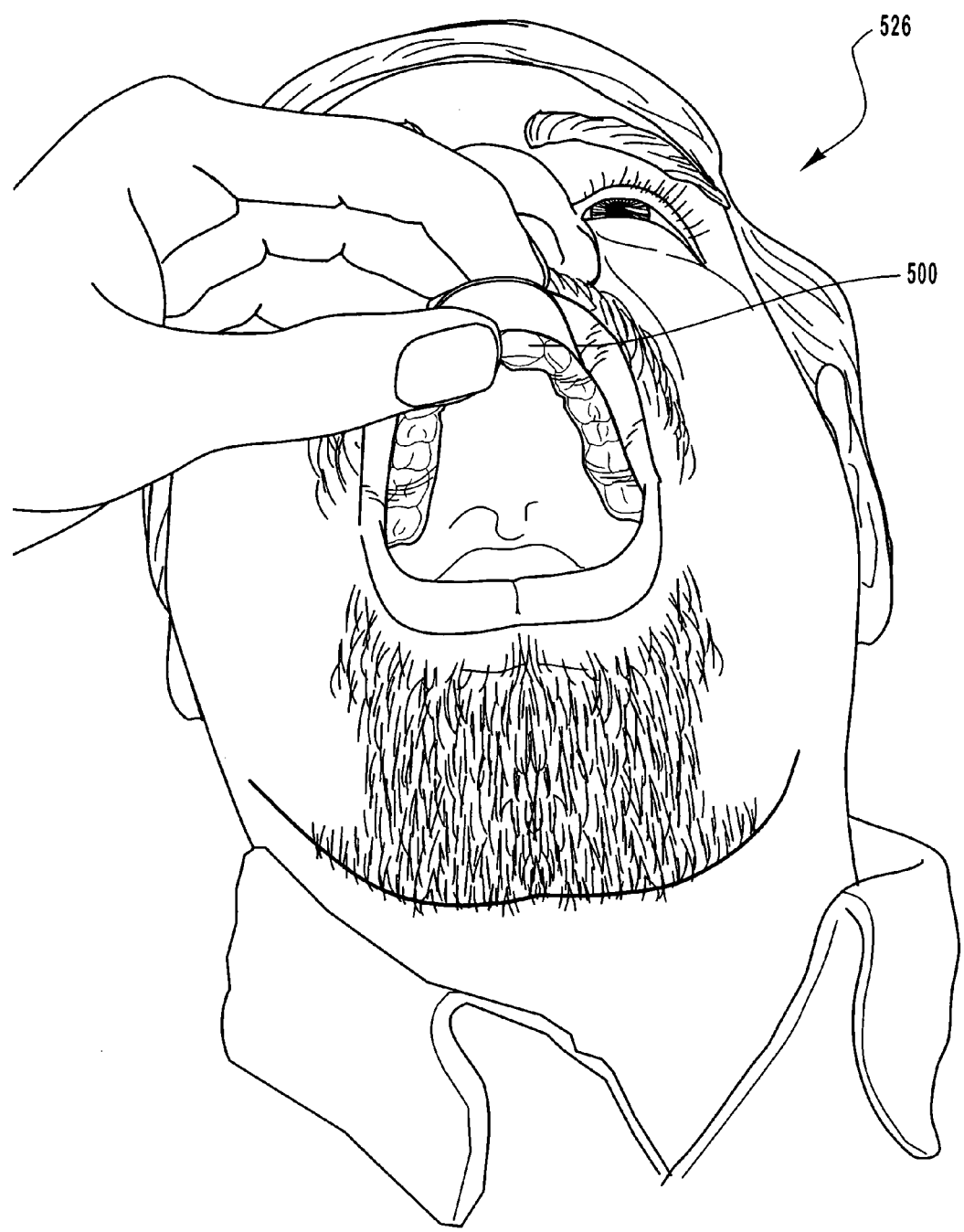
FIG. 5A illustrates a person placing a dental treatment system according to one embodiment of the invention over the upper dental arch.
Figure 5B:
FIG. 5B illustrates the person and dental treatment system of FIG. 5A after the outer support tray has been removed.
Figure 5C:
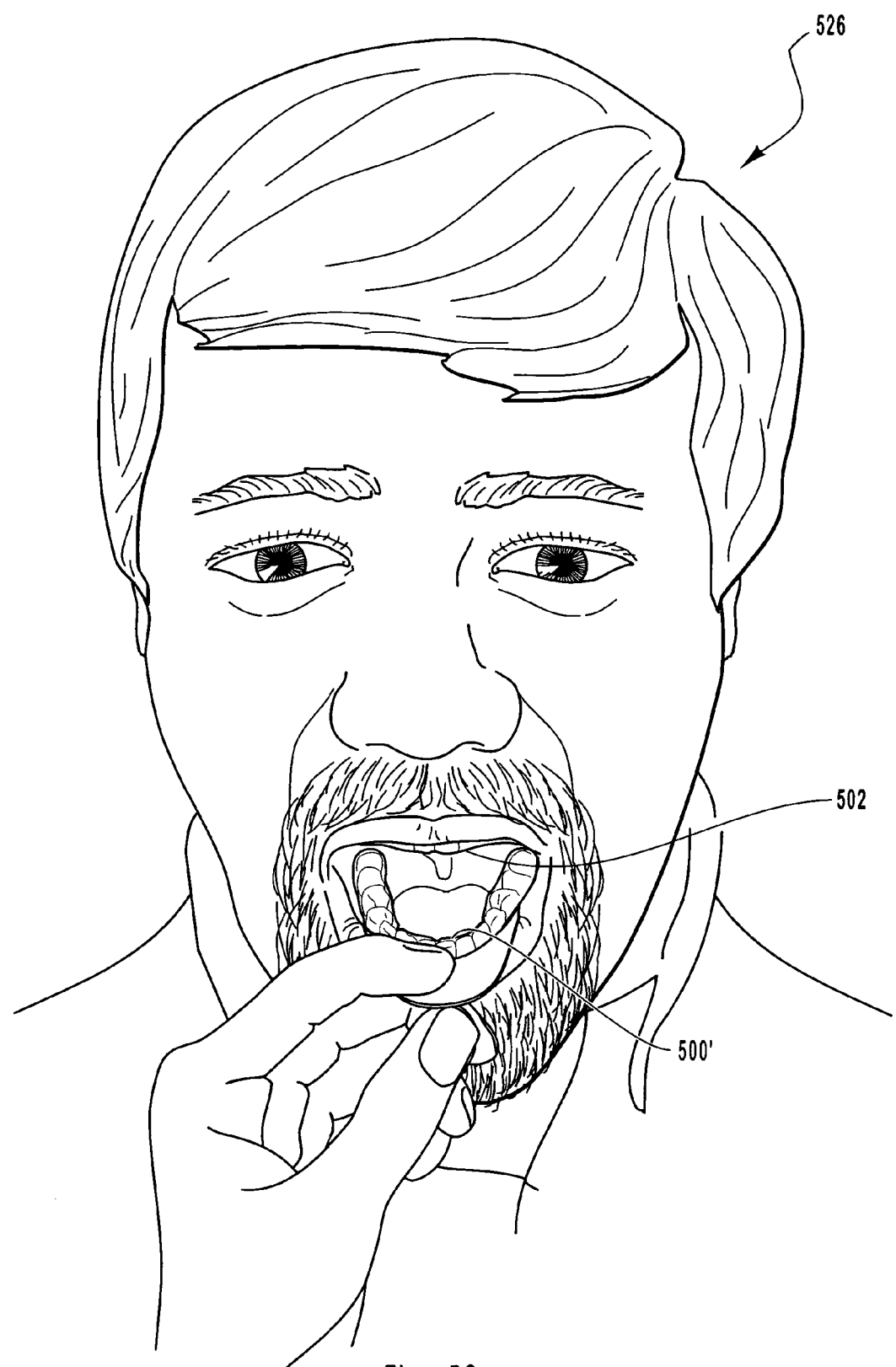
FIG. 5C illustrates a person placing a dental treatment system over the lower dental arch.
Figure 5D:
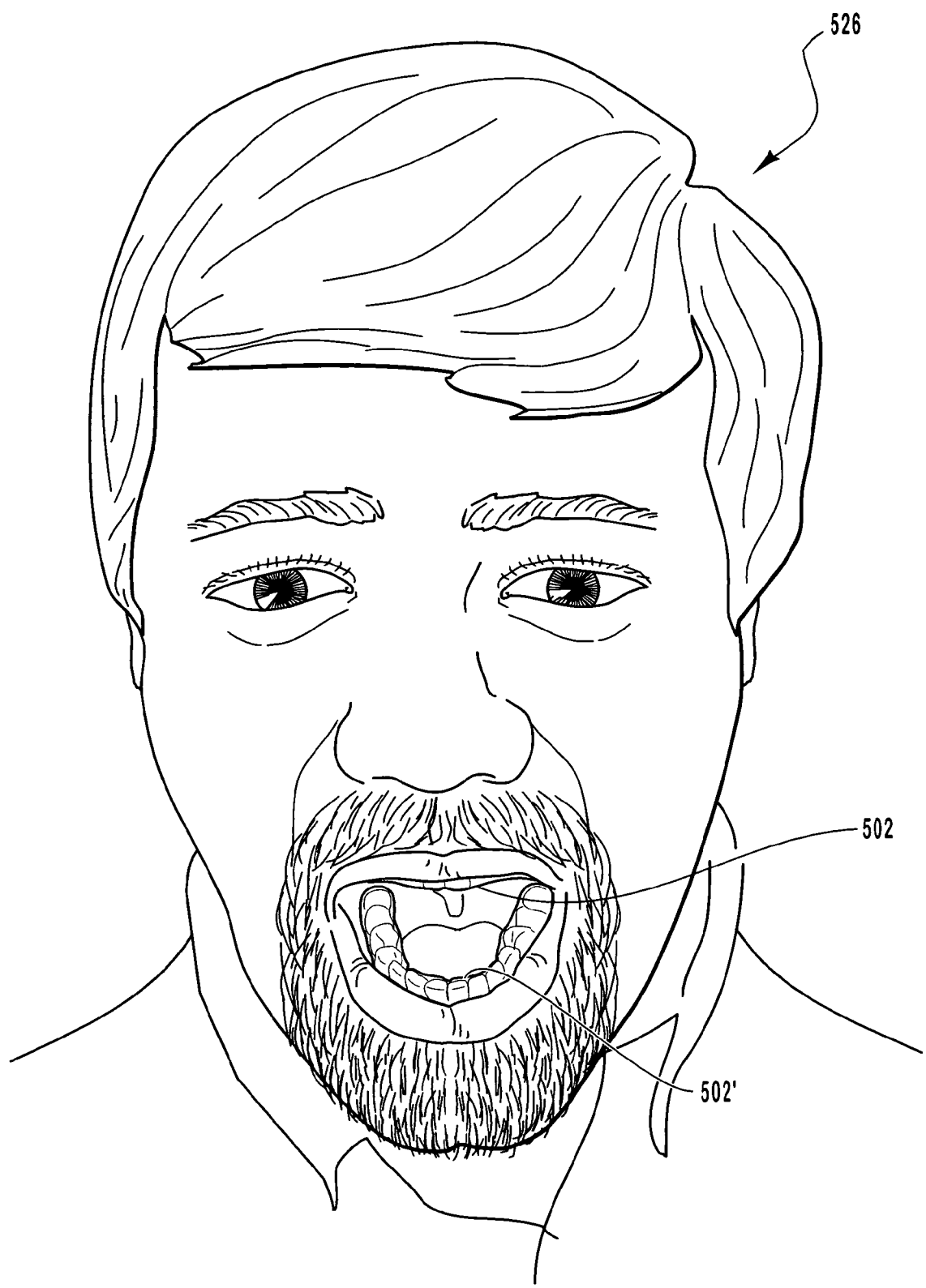
FIG. 5D illustrates the person and dental treatment system of FIG. 5C after the outer support tray has been removed.

FIG. 5A illustrates a person 526 placing a dental treatment system 500 over the person's upper dental arch. FIG. 5B illustrates the person 526 and inner dental treatment tray 502 after the outer support tray 504 has been removed. FIG. 5C illustrates the person 526 placing a dental treatment system 500' over the person's lower dental arch after having placed the inner dental treatment tray 502 of dental treatment system 500 over the upper dental arch. It will be appreciated, however, that the dental treatment systems can be placed over a person's upper and lower dental arches in any desired order. FIG. 5D illustrates the person 526 and inner dental treatment tray 502' after the outer support tray 504' has been removed.

To remove the inner dental treatment tray after treatment, a user can pry open a corner of the inner dental treatment tray using a fingernail or rigid tool and then pull the remainder off. Any residual dental treatment composition that remains adhered to the person's teeth can be removed by washing or flushing water over the person's teeth, and/or by brushing.

The inner dental treatment tray can be worn for as little as a few minutes and as long as several hours. By way of example, not limitation, a typical treatment session of fast duration may last from about 10 to about 30 minutes. A treatment session of intermediate duration may last from about 30 minutes to about 2 hours. A treatment session of long duration, including professional or overnight treatment while a person is sleeping, may last from about 2 hours to about 12 hours.

Treatment sessions may be repeated as many times as are needed to obtain a desired degree of treatment. A typical treatment regimen will preferably include 1-20 treatment sessions, more preferably 2-15 treatment sessions, and most preferably 3-10 treatment sessions.

IV. Dental Treatment Kits

For convenience of use, multiple dental treatment systems may be packaged together and sold as a kit. In one embodiment, the number dental treatment systems provided with each kit will equal the number of sessions that represent a prescribed bleaching regimen.

To efficiently utilize the space within a kit package, multiple dental treatment systems can be stacked or interested together. The systems can be sealed collectively or individually as desired. A protective package 420 is depicted in FIG. 4.

V. Examples of the Preferred Embodiments

Following is an example of a dental treatment system that has been formulated and manufactured according to the invention. Additional examples of treatment compositions and inner dental treatment trays that may be used are disclosed in U.S. patent application Ser. No. 10/790,446, filed Feb. 19, 2004, and entitled ORAL TREATMENT DEVICES THAT INCLUDE A THIN, FLEXIBLE BARRIER LAYER AND AN ENDOSKELETON TREATMENT OR ADHESIVE COMPOSITION, already incorporated by reference. The exemplary formulations and manufacturing conditions are given by way of example, and not by limitation, in order to illustrate dental treatment systems that have been found to be useful for bleaching a person's teeth. Unless otherwise indicated, all percentages are by weight.

Several inner dental treatment trays were formed from a blend of 80% ethylene vinyl acetate and 20% polypropylene having a thickness of about 0.15 mm, while thicker and more rigid outer support trays were formed from the same EVA/PP blend. A thin layer of glycerin was applied as a weak adhesive to the inside surface of some of the outer support trays, while polyethylene glycol (PEG) was applied as a weak adhesive to the inside surface of the other outer support trays. The inner dental treatment trays were inserted into the outer support trays. The dental treatment systems were placed in a holding device, and a bead of dental treatment composition was applied along the front side wall of each inner dental treatment tray.

The dental treatment systems were tested by placing them over a person's teeth. The weakly adhesive glycerin and PEG helped to maintain the inner dental treatment trays within the outer support trays during positioning over the teeth. The inner dental treatment trays were pressed against the teeth, which caused them to conform to the natural irregularities of the dental arch and adhere to the teeth because of the dental treatment composition. The outer support trays were removed with minimal effort once the inner dental treatment trays had conformed and adhered to the teeth.

The inner dental treatment trays were worn for varying time periods ranging from several minutes to several hours. In some cases a noticeable bleaching effect was detected after just one treatment session (e.g., a 2-hour treatment session). In all cases, noticeable bleaching was detected after 1-3 treatment sessions.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A dental treatment system for use in applying a treatment composition to a person's teeth, comprising:
   an inner dental treatment tray having a tray configuration so as to fit over at least a portion of a person's upper or lower dental arch, the treatment tray having a thickness and flexibility so that it at least partially conforms to the person's dental arch without heating when used in combination with a dental treatment or adhesive composition;
   an outer support tray positioned adjacent to the inner dental treatment tray so as to assist in maintaining the inner dental treatment tray in a desired configuration prior to and during placement of the inner dental treatment tray over the person's teeth; and
   temporary adhesion means for maintaining the outer support tray adjacent to the inner dental treatment tray prior to and during placement of the inner dental treatment tray over the person's teeth, the temporary adhesion means permitting easy removal of the outer tray once the inner tray has been placed onto the teeth so that the outer tray is not worn as the inner tray is conformed and then used during treatment of the teeth.

2. A dental treatment system as recited in claim 1, wherein said outer support tray includes a handle.

3. A dental treatment system as recited in claim 1, said temporary adhesion means comprising a weak adhesive between the inner dental treatment tray and the outer support tray.

4. A dental treatment system as recited in claim 3, wherein said weak adhesive comprises at least one of an adhesive silicon, a sticky polymer in water or another solvent, or a sticky resin.

5. A dental treatment system for use in applying a treatment composition to a person's teeth, comprising:
   an inner dental treatment tray having a tray configuration so as to fit over at least a portion of a person's upper or lower dental arch, the treatment tray having a thickness and flexibility so that it at least partially conforms to the person's dental arch without heating when used in combination with a dental treatment or adhesive composition;
   an outer support tray positioned adjacent to the inner dental treatment tray so as to assist in maintaining the inner dental treatment tray in a desired configuration prior to and during placement of the inner dental treatment tray over the person's teeth; and
   a weak adhesive disposed between the inner dental treatment tray and the outer support tray, the weak adhesive maintaining the outer support tray adjacent to the inner dental treatment tray prior to and during placement of the inner dental treatment tray over the person's teeth, and permitting easy removal of the outer tray once the inner tray has been placed onto the teeth so that the outer tray is not worn as the inner tray is conformed and then used during treatment of the teeth, and wherein the weak adhesive is selected from the group of glycerin, polyethylene glycol, adhesive silicons, petrolatum, mineral oil, sticky polymers combined with water or solvents, sticky resins, or combinations of the foregoing.

6. A dental treatment system as recited in claims 3 or 5, wherein said weak adhesive is water soluble.

7. A dental treatment system as recited in claim 6, said weak adhesive comprising one of glycerin or polyethylene glycol.

8. A dental treatment system as recited in claims 1 or 5, wherein said inner dental treatment tray has a cross-sectional thickness in a range of about 0.01 mm to about 1.5 mm.

9. A dental treatment system as recited in claims 1 or 5, wherein said inner dental treatment tray has a cross-sectional thickness in a range of about 0.015 mm to about 0.5 mm.

10. A dental treatment system as recited in claims 1 or 5, wherein said inner dental treatment tray has a cross-sectional thickness in a range of about 0.025 mm to about 0.2 mm.

11. A dental treatment system as recited in claims 1 or 5, wherein said inner dental treatment tray is sized and configured so as to fit over at least a portion of a person's upper dental arch.

12. A dental treatment system as recited in claims 1 or 5, wherein said inner dental treatment tray is sized and configured so as to fit over at least a portion of a person's lower dental arch.

13. A dental treatment system as recited in claims 1 or 5, further comprising a dental treatment composition.

14. A dental treatment system as recited in claims 1 or 5, wherein said system is contained within a sealed package prior to use.

15. A dental treatment system as recited in claims 1 or 5, said inner dental treatment tray including a front side wall and a bottom wall, said bottom wall including a plurality of cuts positioned so as to help said bottom wall better conform to abrupt changes in the diameter of a person's teeth where the bicuspids and canines meet.

16. A kit for use in bleaching a person's teeth comprising a plurality of dental treatment systems according to claims 1 or 5.

17. In a dental treatment system for use in applying a treatment composition to a person's teeth, the dental treatment system having an inner dental treatment tray with a tray configuration so as to fit over at least a portion of a person's upper or lower dental arch, the treatment tray having a thickness and flexibility so that it at least partially conforms to the person's dental arch without heating when used in combination with a dental treatment or adhesive composition, an outer support tray positioned adjacent to the inner dental treatment tray so as to assist in maintaining the inner dental treatment tray in a desired configuration prior to and during placement of the inner dental treatment tray over the person's teeth, and a weak adhesive disposed between the inner dental treatment tray and the outer support tray, a method for bleaching a person's teeth, comprising:

prior to separation and while held together by the weak adhesive, placing both the inner dental treatment tray and the outer support tray over at least a portion of the person's teeth and then removing the outer support tray;

forming the inner treatment tray to conform it to the teeth; and the dental treatment composition then adhering and retaining the inner dental treatment tray against the person's teeth during the desired time period for treatment.

18. A method for bleaching a person's teeth as recited in claim 17, further comprising removing the outer support tray of said dental treatment system.

19. A method for bleaching a person's teeth as recited in claim 17, further comprising removing the inner dental treatment tray of said dental treatment system.

20. A method for bleaching a person's teeth as recited in claim 19, said inner dental treatment tray being removed about 10 to about 30 minutes after being placed over the person's teeth.

21. A method for bleaching a person's teeth as recited in claim 19, said inner dental treatment tray being removed about 30 minutes to about 2 hours after being placed over the person's teeth.

22. A method for bleaching a person's teeth as recited in claim 19, said inner dental treatment tray being removed about 2 hours to about 12 hours after being placed over the person's teeth.

* * * * *

UNITED STATES PATENT AND TRADEMARK OFFICE
CERTIFICATE OF CORRECTION

| | | |
|---|---|---|
| PATENT NO. | : 7,247,022 B2 | Page 1 of 1 |
| APPLICATION NO. | : 11/047150 | |
| DATED | : July 24, 2007 | |
| INVENTOR(S) | : Allred et al. | |

It is certified that error appears in the above-identified patent and that said Letters Patent is hereby corrected as shown below:

Title Page
Page 2, Column 2, Reference 203/0003421, change "Besenheider" to --Bestenheider--

Column 6
Line 46, remove reference |504|
Line 54, remove reference |504'|.

Signed and Sealed this

Twenty-second Day of July, 2008

JON W. DUDAS
*Director of the United States Patent and Trademark Office*